US00PP34973P2

(12) United States Plant Patent
Young-Bustillo et al.

(10) Patent No.: US PP34,973 P2
(45) Date of Patent: Feb. 14, 2023

(54) PINEAPPLE PLANT NAMED 'DOLE-34'

(50) Latin Name: *Ananas comosus*
Varietal Denomination: Dole-34

(71) Applicant: Dole Food Company, Inc., Charlotte, NC (US)

(72) Inventors: Roberto Antonio Young-Bustillo, La Ceiba (HN); Fernando Alberto Molina-Salinas, La Ceiba (HN); Douglas Neptalí Cárdenas-Cárdenas, La Ceiba (HN); Arnold Valentín Soto-Arrazola, La Ceiba (HN)

(73) Assignee: Dole Food Company, Inc., Charlotte, NC (US)

( * ) Notice: Subject to any disclaimer, the term of this patent is extended or adjusted under 35 U.S.C. 154(b) by 0 days.

(21) Appl. No.: 17/751,070

(22) Filed: May 23, 2022

(51) Int. Cl.
*A01H 5/08* (2018.01)
*A01H 6/22* (2018.01)

(52) U.S. Cl.
USPC ..... Plt./156
CPC ..... *A01H 6/22* (2018.05)

(58) Field of Classification Search
USPC ..... Plt./156
CPC ..... A01H 5/08
See application file for complete search history.

*Primary Examiner* — Kent L Bell
(74) *Attorney, Agent, or Firm* — Klarquist Sparkman, LLP

(57) ABSTRACT

A new pineapple (*Ananas comosus*) variety of the Bromeliaceae family was developed from a cross between the parental hybrid 'Dole-17' and the commercial variety 'Dole-11' and has been designated 'Dole-34'. This new variety differs from its progenitors in bearing a large oval to round shaped fruit with a crown that is lengthened cylindrical with a bunchy top, and with an intense reddish-orange color of the shell. The plant is compact and characterized by long spineless leaves with piping, that are green in color with red mottling. When unripe, fruit shell is dark green turning to uniform reddish-orange color when ripe, and the flesh is sweet and develops a yellow color at maturity. It also shows tolerance to natural flowering differentiation (NDF).

8 Drawing Sheets

Specification includes a Sequence Listing.

Latin name of the genus and species of the plant claimed: *Ananas comosus*.

Variety denomination: 'DOLE-34'.

BACKGROUND OF THE INVENTION

Pineapple is a popular fruit worldwide. There is a continued need for improved varieties, particularly those varieties with different and attractive shell color combined with enjoyable fruit flavor.

BRIEF SUMMARY OF THE INVENTION

The invention refers to a new plant variety of pineapple (*Ananas comosus*) family Bromeliaceae, subclass of Monocotyledons, and named 'Dole-34'. The fruit has a distinctly reddish-orange color of the shell, pleasant-sweet flavor, higher carotenoid content which gives an attractive yellow flesh color, and it produces a large oval to round shaped fruit with a crown that is lengthened cylindrical with a bunchy top different from its progenitors. This new variety is tolerant to natural flowering differentiation (NDF).

The new pineapple (*Ananas comosus*) variety, 'Dole-34', inherited several traits from its female parent including the distinctive reddish color of the shell, spineless green leaves showing anthocyanin pigments, and tolerance to NDF, and from its male side received short peduncle length and high carotenoid content in the pulp. 'Dole-34' shows a more compact plant structure, more intense reddish-orange tone in the shell, and higher Brix compared to its female parent. The uniqueness of 'Dole-34' which makes it different from its progenitors is its large reddish oval-to-round shaped fruit with a crown that is lengthened cylindrical with a bunchy top.

BRIEF DESCRIPTION OF THE DRAWINGS

The accompanying photographs depict the new variety 'Dole-34' and its progenitors: 'Dole-17' and 'Dole-11'.

DETAILED DESCRIPTION OF THE INVENTION

Figure 1A:
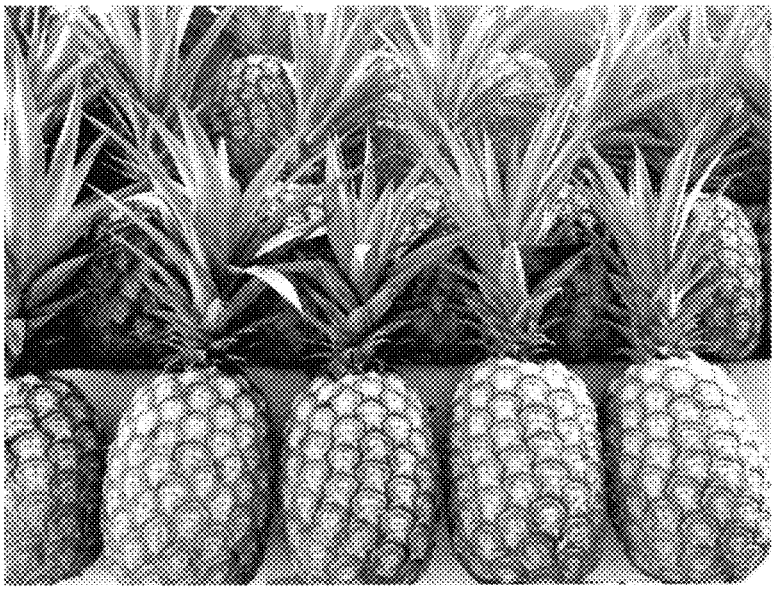
FIG. 1A shows fruit of the female parent 'Dole-17'.
Figure 1B:
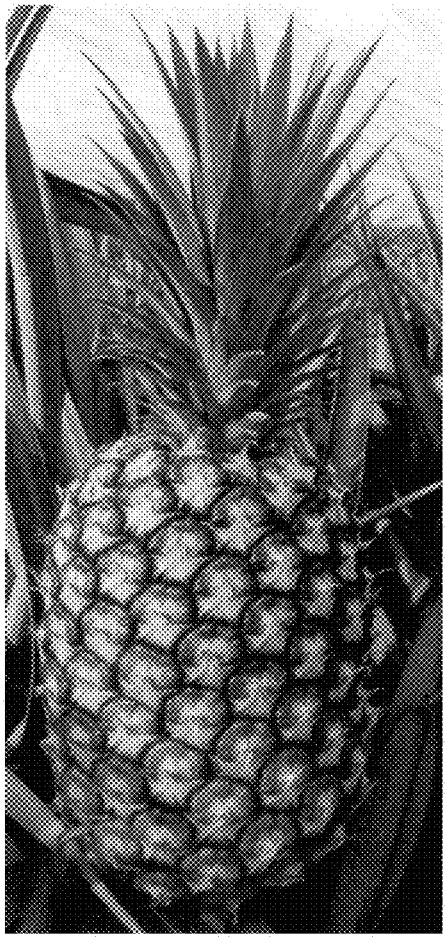
FIG. 1B shows fruit of 'Dole-34'.
Figure 1C:
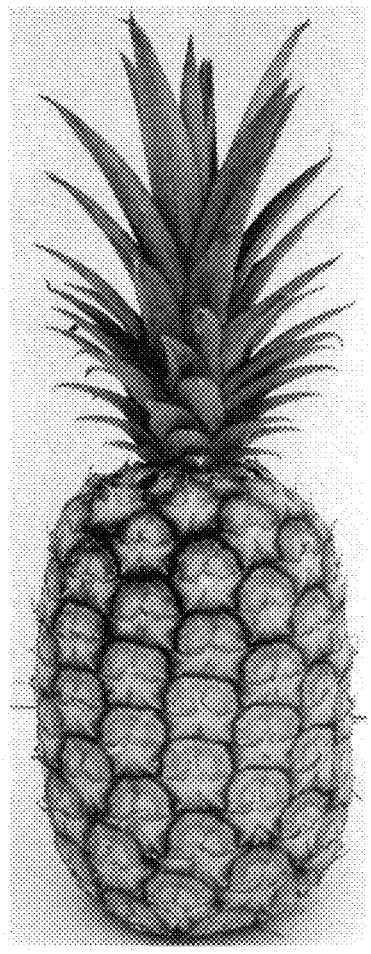
FIG. 1C shows fruit of the male parent 'Dole-11'.
Figure 2:
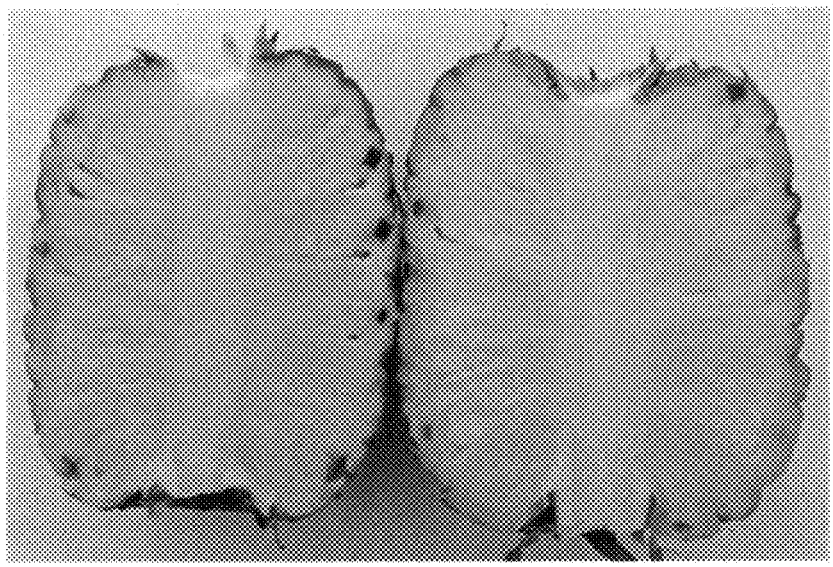
FIG. 2 shows fruit pulp of male parent 'Dole-11' (left) and 'Dole-34' (right).
Figure 3A:
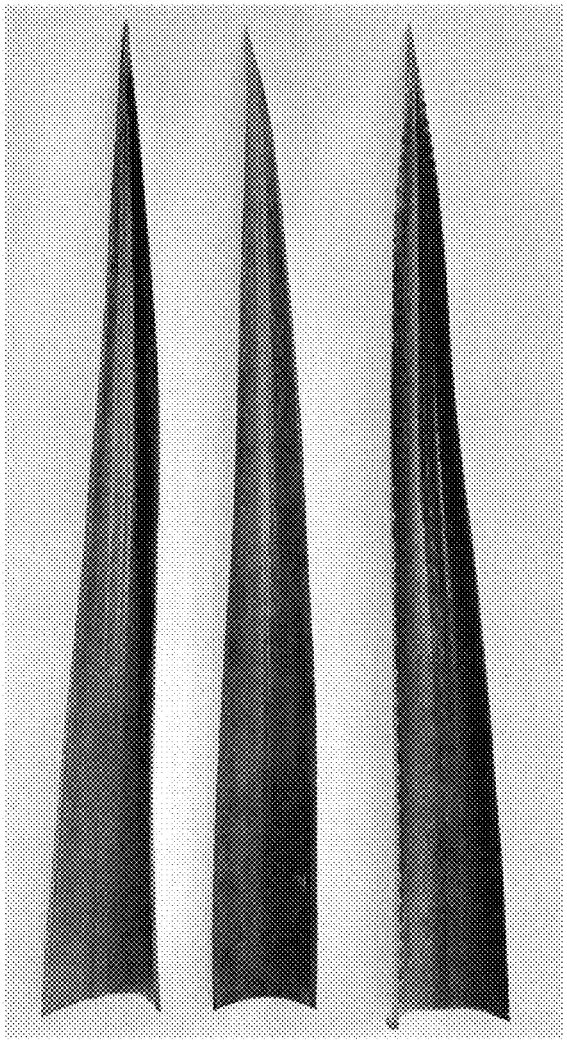
FIG. 3A shows young leaf color of 'Dole-17' (left), 'Dole-34' (Middle), and 'Dole-11' (right).
Figure 3B:
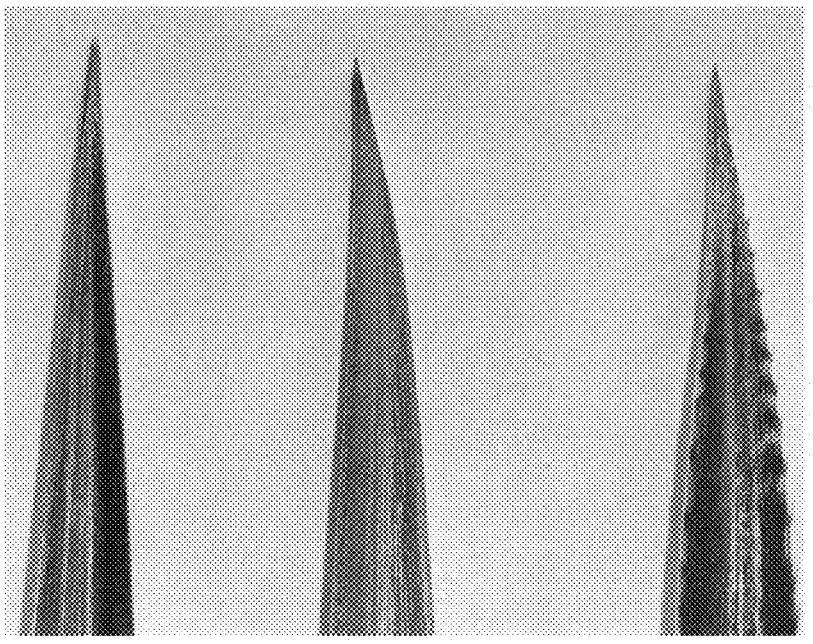
FIG. 3B shows young leaf tip of 'Dole-17' (left), 'Dole-34' (Middle), and 'Dole-11' (right).
Figure 3C:
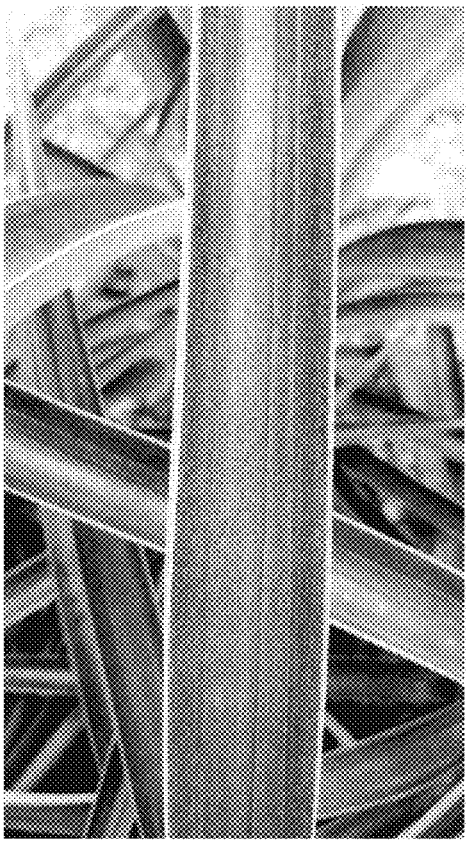
FIG. 3C shows adult leaf margin with piping of 'Dole-34'.
Figure 4:
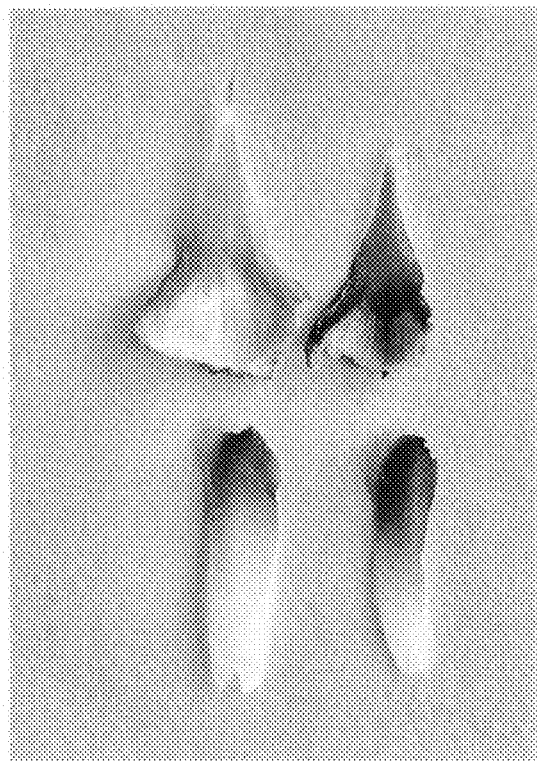
FIG. 4 top shows petal and floral bract of 'Dole-11' (left), 'Dole-34' (right). Bottom shows petal of 'Dole-11' (left), 'Dole-34' (right).
Figure 5A:
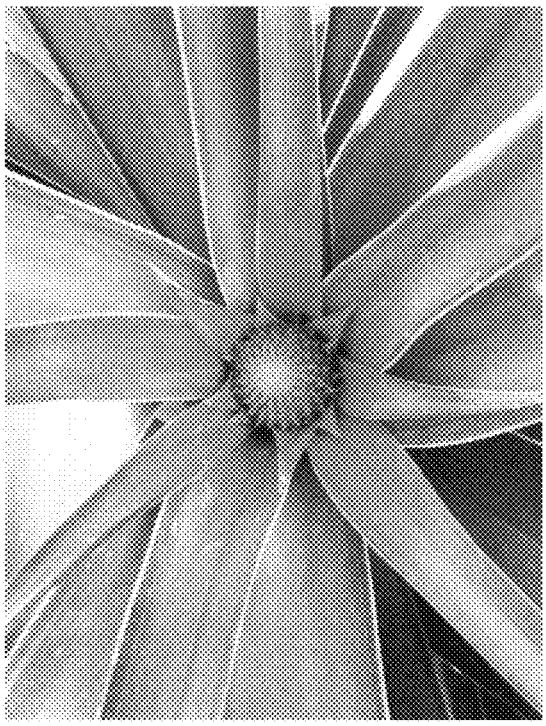
FIG. 5A shows reproductive bottom stage of 'Dole-17'.
Figure 5B:
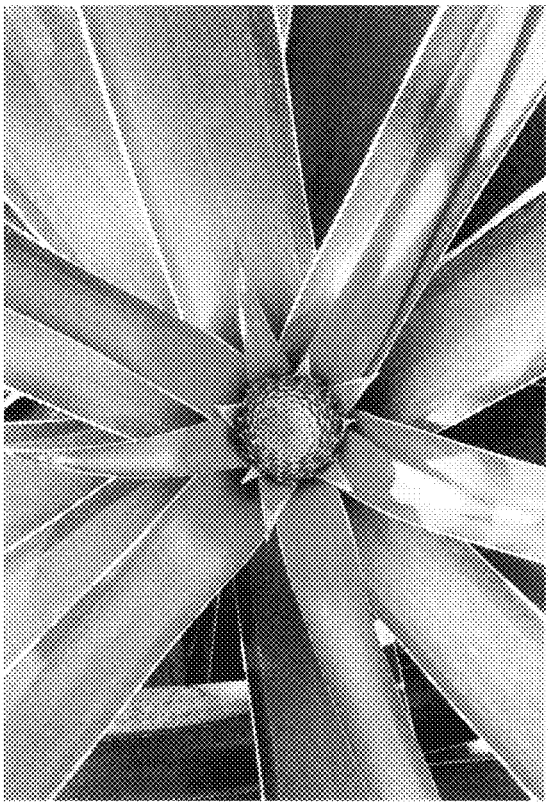
FIG. 5B shows reproductive bottom stage of 'Dole-34'.
Figure 5C:
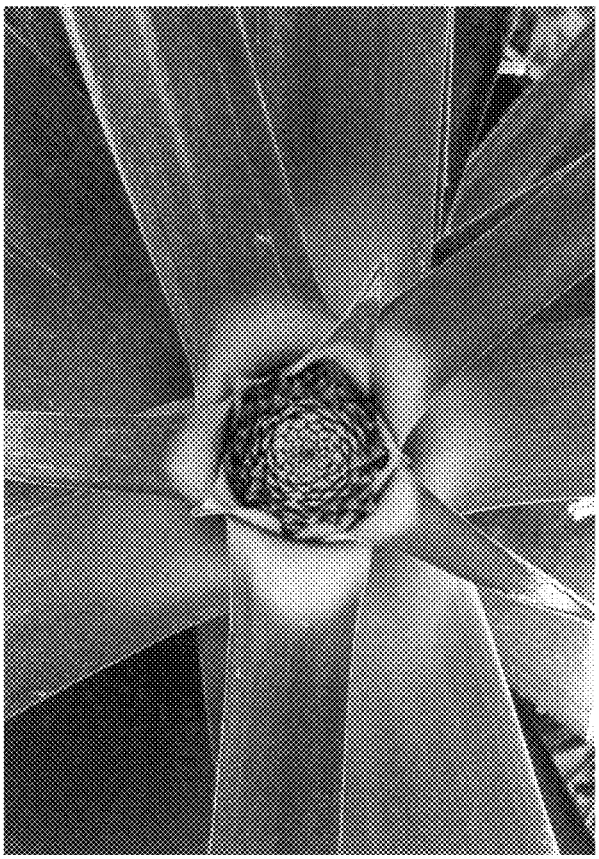
FIG. 5C. shows reproductive bottom stage of 'Dole-11'.

'Dole-34' was originally selected during August 2015 as an individual plant within a segregating population produced from seed from a cross carried out in 2012 between 'Dole-17' (unpatented) and 'Dole-11' (unpatented), and named '1215MC-17/11-025'. Testing and selection of three consecutive asexual generations took place from 2015 through 2021, in Honduras, Central America.

Parental Description: 'Dole-17' used as the female parent was selected after crossing 'Manzana' (a red shell Colombian native cultivar) and 'P-1972' (U.S. Plant Pat. No. 16,396). 'Dole-17' possess a distinctive red shell color derived from its female progenitor 'Manzana'. The plant shows an erect plant habit, upright foliage attitude, long spineless leaves with piping of whitish in color, and green leaves with reddish tones due to the presence of anthocyanin pigments. The inflorescence at bottom stage shows a unique red color. The plant bears a uniform cylindrical and symmetrical fruit with a smooth and thin shell and flat fruitlets or eyes, and it develops many slips by harvest time. Fruit is borne on a long peduncle and the crown is long and conical, with an average weight of 2.0 Kg. 'Dole-17' has unique characteristics such as distinctive fruit aroma with a tendency to acid flavor, and yellow color flesh which varies in intensity depending on the harvest season. Incidence of FCR and marbling is low in 'Dole-17', and it shows high tolerance to natural flowering differentiation (NDF) inherited from its male parent 'P-1972'. 'Dole-17' shows tolerance to FCR (Fruitlet Core Rot) caused by *Fusarium moniliforme*, Blackheart, and Root Rot caused by *Phytophtora cinnamomi.*

'Dole-11' used as the male parent, was derived from crossing hybrid clones 58-1184 and 59-443. 'Dole-11', also known as Tropical Gold® pineapple, is a popular commercial variety appreciated for its yellow and golden yellow shell and pulp color when ripen respectively. Regularly, leaf margins in 'Dole-11' are devoid of spines: however, spines may be present, and their abundance and distribution may vary depending on the environmental conditions. The inflorescence at bottom stage shows a unique green-yellow color. Fruit is mostly conical to cylindrical-sharp taper in shape, with a long conical and attractive crown, and weighing approximately 1.9 Kg. The flesh in 'Dole-11' is smooth in texture, with small to intermediate amount of fiber, and with high content of vitamin C. Brix/Acid ratio ranges from 28°-35°, favoring a pleasant and mostly sweet flavor. 'Dole-11' is resistant to both FCR (Fruitlet Core Rot) caused by *Fusarium moniliforme*, and Blackheart, but it is highly susceptible to Root Rot caused by *Phytophtora cinnamomi.*

This breeding effort aimed to produce a fresh fruit variety with high yield potential, distinctive red shell color, pleasant aroma with sweet pulp flavor, and tolerant to natural flowering differentiation. The development of the new variety started during 2012 in the North coast of Honduras (USDA Hardiness Zone: approximately 13 B). A segregating population was produced by cross-pollinating flowers of 'Dole-17' with pollen taken from plants of the variety 'Dole-11'. The first plant selection was practiced in year 2015 and was identified as '1215MC-17/11-025' later named 'Dole-34'. Genetic stability of this selection was evaluated during three consecutive asexual generations which took place from 2015 through 2021 in El Porvenir, Atlántida. Different methods of asexual propagation were used for variety multiplication, i.e., stem cuttings, slips, suckers, gouging of fruit crowns, and tissue culture derived plants. 'Dole-34' shows unique characteristics such as spineless leaves of green with red mottling colors showing piping, a large oval to round shaped fruit with a crown that is lengthened cylindrical with a bunchy top, a reddish inflorescence at bottom stage, a distinctive reddish-orange color of the shell, and a balanced sweet/acid pulp flavor particularly during the dry warm season. Conducive NDF conditions occurring in the North Coast of Honduras during three consecutive winter seasons revealed that the new pineapple hybrid 'Dole-34' is tolerant to natural flowering. The new variety is stable and has reproduced true to type in three successive generations of asexual reproduction.

DETAILED BOTANICAL DESCRIPTION OF THE PLANT

The following is a description of the new plant variety based on observations made prior to forcing in December of 2019, after forcing in February of 2020, and at harvesting in September through October of 2020, grown in the North Coast of Honduras (15 degrees 44 minutes latitude north, and 86 degrees 53 minutes longitude west). The average temperature in the North Coast Honduras is 26° C., with 3,542-mm of annual average precipitation. The Munsell Color Chart was used for all color designations (Munsell Book of Color Gretag Macneth LLC, 617 Little Britain Road, New Windsor, N.Y. 12553-6148).

Name: *Ananas comosus* (L.) Men. Var. 'Dole-34', family Bromeliaceae, subclass Monocotyledons.

Parentage:

I. *Seed parent.*—Variety 'Dole-17'.

II. *Pollen parent.*—Commercial variety 'Dole-11'.

Classification:

I. *Botanic.*—Family: Bromeliaceae. Subfamily: Bromeliacidae. Genus: *Ananas*. Species: *comosus*. Cultivars: 'Dole-17' x 'Dole-11'.

II. *Commercial.*—Bromeliad fruit plant. General form: During the vegetative stage, 'Dole-34' has a normal posture with an open foliage attitude and consists of a compact rosette of overlapping sessile leaves arising from a central stem and surrounding a composite inflorescence prior anthesis. Production of offshoots (suckers, hapas and slips) is usually absent, but depending on season slips may vary from 1 to 2 per plant. Plant height at forcing time was on average 138.2±2.2 cm, but it may vary depending on growing conditions. Plant diameter was 5.2±0.6 cm, measured at the base and at forcing time in a 3.1±0.3 Kg plant.

Stems: Stem is upright, sheathed by overlapping leaves arranged in acropetal fashion, forming a heart shape stem. The stem color is greyish (5Y 8/2 to 8/4). Stem length was 56.6±5.5 cm, measured from the plant's base to the peduncle's base.

Leaves:

I. *General.*—leaves are sessile, trough shaped, tapered from base to tip, elongated and succulent, with acuminate apex, and forming a rosette with a 5/13 phyllotaxy. Depending on growing conditions, the average number of leaves per plant is 80.8±4.7 The breakage resistance of the leaf is hard, and foliage attitude is open (Descriptors for Pineapple, IBPGR, Rome 1991). Trichomes are present in the abaxial side of the leaves.

II. *Color*.—The color of the upper surface of the D leaf is green (5GY 6/6, 5/6, 4/6) with red mottling (5R 5/6, 4/4, 4/6) and in the lower surface is light green (5GY 8/2, 8/4, 7/4).

III. *Margins*.—The leaves are completely spineless showing the presence of piping, which is a narrow silvery-white (2.5GY 8/2) stripe extended over the adaxial surface along the leaf edge. Margin color is green but darker than the middle section (5GY 4/4, 4/6, 4/8). The longest leaf thickness is on average 0.96±0.11 mm at middle section.

IV. *Leaf size*.—Depending on growing conditions, measurements taken on D leaf may vary from 102±5.7 to 111.2±5.1 cm in length, and 5.7±0.4 to 6.8±0.5 cm in width at middle section.

Inflorescence:

I. *General*.—Pineapple inflorescence of composite flower, with self-incompatible individual bi-sexual flowers containing three sepals (9.3±0.5 mm in length), three petals (20.9±0.7 mm in length, 6.9±0.5 mm wide), six syngenesious stamens (15.0±0.6 mm in length and cream in color), the yellowish (2.5 Y 8/10) anthers are heart-shaped with a dorsifixed attachment (2.91±0.4 mm in length) and bearing abundant pollen. The gynoecium is composed of an axile ovary (three carpels 5 to 6 mm in length) of cream color and a whitish style (length 16.3±0.4 mm) with a lobed-shaped stigma. The inflorescence is borne in a long conical and slender peduncle (43.5±1.2 cm in length, and 1.9±0.2 cm in diameter at middle section). The number of days to flowering after forcing is as follows: 42 days to the presence of a distinctive reddish floral bud, and 66 days to mid flower. The inflorescence length at mid flower stage is 10.0±0.5 cm. The inflorescence diameter at mid flower stage is 6.3±0.4 cm.

II. The penduncle bract has a lanceolate form, with an acute apex, acuminate base, and entire margins. Bract color in the adaxial side is green at the tip (7.5 GY 4/4, 4/6) and pink to orange at the base (2.5 R 6/10, 5/10 and 10 R 6/8, 6/10). The bract color in the abaxial side is opaque green (7.5 GY 8/4, 7/4, 7/6). The average number of peduncle bracts is 19.6±0.6, with the longest bract length of 58.1±5.4 cm, and width of 3.4±0.3 cm, and the shortest bract length of 2.4±0.2 cm, and width of 2.0±0.3 cm. The floral bract, which covers ⅔ of the flower, is of aristate apex and truncate base. The floral bract is 18.8±0.8 mm in length, 14.7±0.7 mm wide and has a smooth edge. The floral bract color at the adaxial side of the tip is reddish (2.5 R 4/10, 5 R 4/10, 3/10), and greenish at the base (2.5 GY 8/4, 8/6, 7/4, 7/6). The floral bract at the abaxial side is pinkish (5 R 8/4, 7/4, 7/6).

III. Petals have entire margins with an oblong shape and a closed orientation. The apex is subacute, and the base is truncate. Petal color is white at the base, pink in the middle section (5 RP 8/6, 7/6, 7/8) and deep purple at the tip in both surfaces (5 RP 4/10, 4/12, 3/10).

IV. The sepals have entire margins with an orbicular shape and obtuse apex. In the adaxial side the coloration of the tip (5 R 7/8, 6/10, 10 R 6/10), middle (5 R 4/6, 3/4) and base (7.5 GY 6/6, 6/8, 6/10) vary from brownish red to greenish-green. In the abaxial side the coloration is pinkish orange (5 R 7/8, 6/8, 6/10: 10 R 7/8, 6/8, 6/10) with trichomes.

Fruit:

I. *Fruit shape*.—The fruit is oval to round shaped with 16.5±1.3 cm in height, and with a diameter of 12.6±0.9 cm at middle part, and the shell is smooth and thin (2-3 mm thick). The number of fruitlets is 138.4±7.0, averaging 8±0.5 spirals per fruit, and 18.4±1.3 fruitlets in the longest spiral. The coloration of the fruitlet is orange reddish (5 YR 7/10, 6/8, 6/10, and 5 R 5/10, 4/10, 10 R 6/10, 5/10, 4/10) and it has a mamiform shape apex. The fruitlet length is 5.6±1.4 mm and 2.5±0.3 mm in diameter.

II. Fruit and crown average heights are 17.3±0.5 cm and 19.0±6.1 cm respectively for a fruit/crown ratio of 0.91. Mean fruit weight with crown is 2.3±0.5 Kg.

III. *Crown characteristics*.—The crown is lengthened cylindrical with a bunchy top, with weight ranging from 200 to 300 g and 16.6±0.6 cm in diameter. Leaf color is green (5 GY 6/6, 5/6, 4/6) with red mottling (5R 5/6, 4/4, 4/6) and in the lower surface is light green (5 GY 8/2, 8/4, 7/4). Leaves are spineless and smooth, having an acute apex and acuminate base, with a narrow silvery-white (2.5 GY 8/2) piping in its margins, which are green but darker (5 GY 4/4, 4/6, 4/8) than the middle section of the leaf. The crown has an average amount of 140±2 leaves. Leaf length and width (cm) vary at the lower (5.0±0.4; 2.7±0.2), middle (9±0.9; 3.1±0.1) and upper part (13.6±1.8; 3±0.7) of the crown.

IV. *Flesh and juice characteristics* (*grade* 5).—The flesh is compact, smooth texture with low fibers and distinct aroma. Core diameter is 3.7±0.2 cm. Flesh color is yellow (2.5Y 8/8, 8/10; 5Y 8/8, 8/10, 8/12), and with acceptable translucency appearance. Table 1 compares fruit quality values for 'Dole-34' and its progenitors.

TABLE 1

Comparison of internal fruit quality characteristics at maturity grade 3, between 'Dole-34' and parental varieties, under the North Coast of Honduras conditions during September of 2020.

| Pineapple Variety | Brix (%) | Acid % (g/100 ml Citric acid) | Carotenoids (ppm) | Ascorbic Acid (mg/ml) |
|---|---|---|---|---|
| 'Dole-34' | 14.0 ± 1.6 | 0.73 ± 0.2 | 10.6 ± 4.3 | 0.59 ± 0.2 |
| 'Dole-11' | 15.0 ± 1.5 | 0.62 ± 0.1 | 10.7 ± 2.2 | 0.90 ± 0.1 |
| 'Dole-17' | 13.1 ± 0.1 | 0.78 ± 0.0 | 7.3 ± 0.4 | 0.47 ± 0.0 |

V. *Peduncle*.—Fruit develops from the apical meristem of the plant on a peduncle, usually 43.5±1.2 cm in length, and 1.9±0.2 cm in diameter. The peduncle has a waxy texture due to the presence of trichomes and it has a greenish color at the middle section (2.5 GY 8/10, 8/12; 5 GY 7/8, 5/8, 4/8). — VI. Table 2 compares the tolerance of 'Dole-34' and known varieties to certain pests, diseases, and other disorders.

TABLE 2

Tolerance comparisons of 'Dole-34' and known varieties to certain pests, diseases, and other disorders when grown under the North Coast of Honduras conditions.

| Condition | 'Dole-34' | 'Dole-11' | 'Dole-17' |
|---|---|---|---|
| Phytophtora | moderate | high | high |
| Erwinia | moderate | high | moderate |
| Army worm | none | none | none |
| Mealybug (*pseudococcus brevipes*) | none | none | none |
| Natural Flowering | moderate | low | high |
| Translucency | high | high | high |
| Fruitlet Core Rot | high | high | high |
| Internal Brown Spot | high | high | high |
| Shell cracking | high | high | high |
| Open eye | high | high | high |
| Crown defects | high | moderate | high |
| **Condition** | **'P-1972'** | **'Dole-14'** | **'Champaka'** |
| Phytophtora | moderate | moderate | high |
| Erwinia | moderate | moderate | high |
| Army worm | low | low | low |
| Mealybug (*pseudococcus brevipes*) | low | low | low |
| Natural Flowering | high | high | moderate |
| Translucency | moderate | high | high |
| Fruitlet Core Rot | high | high | moderate |
| Internal Brown Spot | high | high | low |
| Shell cracking | moderate | high | high |
| Open eye | moderate | high | high |
| Crown defects | high | high | low |

'Dole-11': unpatented; 'Dole-17': unpatented; 'P-1972': U.S. Plant Pat. No. 16,396: 'Dole-14': U.S. Plant Pat. No. 20,885; 'Champaka': unpatented

MOLECULAR (DNA) MARKERS FOR 'DOLE-34' AND PARENTS

Four indel DNA markers were developed using a combination of primers (Table 3) for distinguishing between 'Dole-34' and its progenitors 'Dole-17' and 'Dole-11'.

TABLE 3

Primers used for generating DNA markers for discriminating between 'Dole-34' and its progenitors.

| Primer Name | Primer Sequence (SEQ ID NO:) |
|---|---|
| P1_Forward | AACTGGTATTTGTATTAGCTAAAAAGG (1) |
| P1_Reverse | ATAAACTCCCATGCGTACACT (2) |
| P2_Forward | GATAATCGAAAAGATGTCACTTTACG (3) |
| P2_Reverse | AGTTAATTGTGGATAAGTGGTGG (4) |
| P3_Forward | ATGTGACAAGCGAAGTCAAGC (5) |
| P3_Reverse | ATGCATAATGTGTTCAGTGTTGCT (6) |
| P4_Forward | GGAAAACCAGACACTCCTT (7) |
| P4_Reverse | GATCTGGGCCAACATATGCT (8) |

The PCR program for generating the banding patterns was as follows: First denaturing cycle at 98° C. for 50 seconds, forty cycles of denaturing at 98° C. for 10 seconds, primer annealing at 56° C. for 15 seconds, and extension at 72° C. for 12 seconds, a final extension at 72° C. for 3 minutes, and finally hold at 4° C. PCR products were analyzed by 3% agarose electrophoresis. The assignment of genotype A, B and H was as follows:

A: Single, longer PCR product (230 bp-250 bp)

B: Single, shorter PCR product (200 bp-230 bp)

H: Multiple PCR products between 200 bp to 300 bp in size

Figure 6:
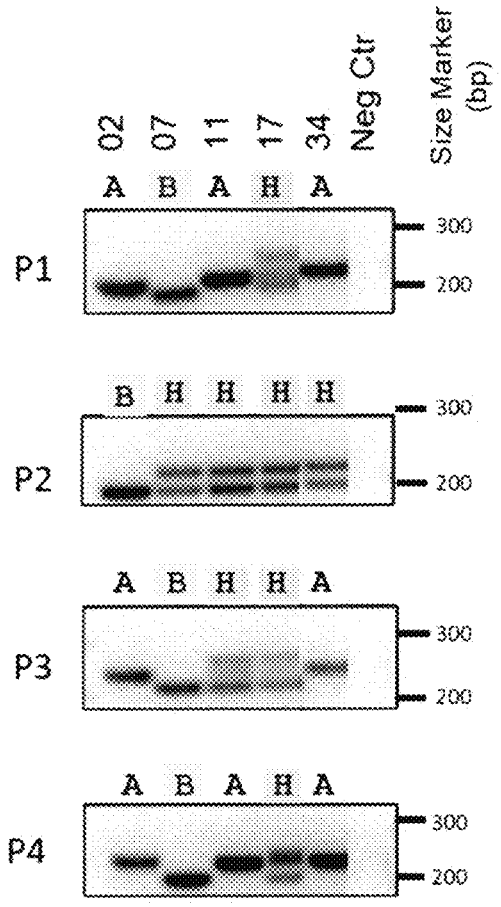
FIG. 6 shows PCR products identified in DNA obtained from pineapples 02 ('P-1972', U.S. Plant Pat. No. 16,396), 07 ('Manzana', unpatented), 11 ('Dole-11', unpatented), 17 ('Dole-17', unpatented), and 34 ('Dole-34').

As shown in FIG. 6, the following unique pattern code combining PCR products was identified:

02 ('P-1972'): ABAA 07 ('Manzana'): BHBB 11 ('Dole-11'): AHHA 17 ('Dole-17') HHHH 34 ('Dole-34'): AHAA

SEQUENCE LISTING

```
<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: primer

<400> SEQUENCE: 1

aactggtatt tgtattagct aaaaagg                                27


<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
```

-continued ataaactccc atgcgtacac t 21

<210> SEQ ID NO 3
<211> LENGTH: 26
<212> TYPE: DNA
<213> ORGANISM: Artificial Sequence
<220> FEATURE:
<223> OTHER INFORMATION: primer

<400> SEQUENCE: 3 gataatcgaa aagatgtcac tttacg 26

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4 agttaattgt ggataagtgg tgg 23

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5 atgtgacaag cgaagtcaag c 21

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6 atgcataatg tgttcagtgt tgct 24

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7 ggaaaaccag acactcctt 19

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8 gatctgggcc aacatatgct 20

We claim:

1. A new and distinct variety of pineapple plant designated 'Dole-34' substantially, as shown and described herein.

* * * * *